United States Patent
Williams et al.

(10) Patent No.: US 6,649,406 B1
(45) Date of Patent: Nov. 18, 2003

(54) DEVICE FOR PROPAGATION AND STORAGE OF MICROORGANISMS

(75) Inventors: Michael G. Williams, Vadnais Heights, MN (US); Karen E. Hesselroth, Stillwater, MN (US); Raj Rajagopal, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/541,416

(22) Filed: Apr. 3, 2000

Related U.S. Application Data

(60) Provisional application No. 60/167,036, filed on Nov. 23, 1999.

(51) Int. Cl.[7] .............................. C12M 1/32; C12Q 1/24
(52) U.S. Cl. ................ 435/309.4; 435/30; 435/32; 435/39; 435/287.9; 435/288.3; 435/305.4
(58) Field of Search .............................. 435/29, 30, 32, 435/39, 287.1, 287.2, 287.9, 288.3, 288.7, 305.1, 305.4, 307.1, 309.4, 805, 810

(56) References Cited

U.S. PATENT DOCUMENTS

| | | | |
|---|---|---|---|
| 4,565,783 A | | 1/1986 | Hansen et al. |
| 5,089,413 A | | 2/1992 | Nelson et al. |
| 5,137,812 A | | 8/1992 | Matner |
| 5,232,838 A | | 8/1993 | Nelson et al. |
| 5,443,963 A | * | 8/1995 | Lund ........................... 435/34 |
| 5,601,998 A | | 2/1997 | Mach et al. |
| 5,869,321 A | | 2/1999 | Franklin |
| 5,958,675 A | * | 9/1999 | Wicks et al. ................. 435/5 |
| 6,022,682 A | * | 2/2000 | Mach et al. .................. 435/4 |

FOREIGN PATENT DOCUMENTS

EP      0 168 238 A2      1/1986

* cited by examiner

*Primary Examiner*—William H. Beisner
(74) *Attorney, Agent, or Firm*—Nancy M. Lambert

(57) ABSTRACT

Devices for the propagation or storage of microorganisms are described. Generally, the devices include first and second layers that are separable from each other. The first layer includes a gelling agent and microbial growth medium and the second layer comprising a galling agent. The devices further include an indicator and a corresponding inducer, each of which may be included in the first layer, second layer, or both.

38 Claims, 1 Drawing Sheet

DEVICE FOR PROPAGATION AND STORAGE OF MICROORGANISMS

CROSS REFERENCE TO RELATED APPLICATIONS

This application claims priority from U.S. Provisional Application Serial No. 60/167,036, filed Nov. 23, 1999.

TECHNICAL FIELD

This invention relates to the field of molecular biology. In particular, it relates to processes involving the propagation and analysis of microorganisms including recombinant microorganisms.

BACKGROUND

Rehydratable dry film plating media have been described (e.g., U.S. Pat. No. 4,565,783) for the detection and enumeration of microorganisms in food or other samples. For example, dry film plating media technology has been used for testing for a particular antigenic strain of pathogenic *E. coli*. See, for example, U.S. Pat. No. 5,137,812. Typical devices that use dry film media technology contain a cold-water-soluble gelling system, which allows for addition of a 1 ml aqueous sample. Such devices promote the growth of target organisms within the device under suitable incubation conditions, and also provide a detection system within the device to allow for visualization and enumeration of the colonies growing in the device. These devices have particular utility within the food processing industry, where the detection and enumeration of specific target organisms or indicator organisms serves as an index of food quality and/or safety.

In contrast to microbiological testing, where organisms are seldom stored for future use, it is common among molecular biologists to store recombinant microorganisms in broth cultures or on semisolid media for future use. Additional steps are needed to transfer the recombinant microorganisms from the primary plating medium to the storage medium and, frequently, an additional growth period (16–24 hours) is needed to incubate the storage medium before it is placed at the storage temperature.

A disadvantage of semisolid medium (agar) when used for culture storage is the tendency for the moisture to evaporate from the gel. In the case of unsealed petri dishes, this results in the dehydration of the agar and the death of the cultures. In the case of sealed petri dishes, this results in the condensation of moisture onto the plastic or glass dishes, which may result in moisture spreading across the surface of the agar and cross-contamination of colonies on the plate. Furthermore, it is not possible to freeze cultures on agar plates because the agar tends to develop ice crystals on the surface and/or split when frozen. Both of these features increase the probability of colony cross-contamination, which is undesirable when trying to maintain pure clones of recombinant organisms. In addition, a primary objective of plating recombinant organisms is to perform genetic analyses, which typically results in the destruction of the cells. Thus, it is usually necessary to pick each colony and "replicate" it in broth or semisolid media before using the remnants of the colony for the genetic analysis.

SUMMARY

The invention described herein is based on novel formulations of dry film plating media that provide unique properties to a device for the propagation or storage of microorganisms. Upon opening the device containing such a formulation, a portion of a colony growing on the plate transfers to both films, providing two replicates of each clone. In addition, colonies on the plate are larger than those growing on commercially available Petrifilm™ plates. These properties offer several advantages to molecular biologists and others who need to analyze or subculture bacterial colonies grown on semisolid media.

In one aspect, the invention features a device for the propagation or storage of microorganisms. The device includes first and second layers, wherein the first layer includes a gelling agent and microbial growth medium and the second layer includes a gelling agent, wherein the device further includes an indicator and a corresponding inducer, and wherein the first and second layers are separable from each other. The first or second layers can be rehydratable. At least 80% (e.g., 85% or 95%) of visible microorganism colonies can partition to form replicates on the first and the second layers upon separation of the layers. The replicates on the first or second layer are detectable by magnified or unmagnified visual inspection, or by genetic analysis. Detection by genetic analysis can include hybridization, polymerase chain reaction, plasmid restriction analysis, or expression screening techniques.

Replicates on the first or second layer are viable. The gelling agent of the first or second layers can be guar gum, xanthan gum, locust bean gum, polyvinyl alcohol, carboxymethylcellulose, alginate, polyvinylpyrrolidone, gellan or low monomer content polyacrylic acid. Guar gum is particularly useful.

The microbial growth medium can include a detergent such as an ionic detergent, e.g., deoxycholate, bile salts or lauryl sulfate or a salt. The first layer further can include a selectable agent such as an antibiotic or an amino acid deficiency. Indicators can be precipitable or chromogenic (e.g., 5-bromo-4-chloro-3-indoxyl-β-D-glucuronic acid, L-Alanine-5-bromo-4-chloro-3-indoxyl ester (trifluoroacetate salt), 5-bromo-4-chloro-3-indoxyl-1-acetate, 5-bromo-4-chloro-3-indoxyl-3-acetate, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl butyrate, 5-bromo-4-chloro-3-indoxyl caprylate, 5-bromo-4-chloro-3-indoxyl-β-D-cellobioside, 5-bromo-4-chloro-3-indoxyl-α-L-fucopyranoside, 5-bromo-4-chloro-3-indoxyl-β-D-fucopyranoside, 5-bromo-4-chloro-3-indoxyl-β-L-fucopyranoside, 5-bromo-4-chloro-3-indoxyl-α-D-galactopyranoside, 5-bromo-4-chloro-3-indoxyl-β-D-galactopyranoside, 5-bromo-4-chloro-3-indoxyl-α-D-glucopyranoside, 5-bromo-4-chloro-3-indoxyl-β-D-glucopyranoside, 5-bromo-4-chloro-3-indoxyl-β-D-glucuronic acid (cyclohexylammonium salt), 5-bromo-4-chloro-3-indoxyl-β-D-glucuronicacid (sodium salt), 5-bromo-4-chloro-3-indoxyl myo-inositol-1-phosphate (ammonium salt), 5-bromo-4-chloro-3-indoxyl-α-D-maltotriose, 5-bromo-4-chloro-3-indoxyl myristate, 5-bromo-4-chloro-3-indoxyl-α-D-mannopyranoside, 5-bromo-4-chloro-3-indoxyl-nonano ate, 5-bromo-4-chloro-3-indoxyl oleate, 5-bromo-4-chloro-3-indoxyl palmitate, 5-bromo-4-chloro-3-indoxyl phosphate (di{2-amino-2-methyl-1,3-propanediol}salt), 5-bromo-4-chloro-3-indoxyl phosphate (dilithium salt hydrate), 5-bromo-4-chloro-3-indoxyl phosphate (dipotassium salt), 5-bromo-4-chloro-3-indoxyl phosphate (disodium salt sesquihydrate), 5-bromo-4-chloro-3-indoxyl phosphate (potassium salt), 5-bromo-4-chloro-3-indoxyl phosphate (p-toluidine salt), 5-bromo-4-chloro-3-indoxyl sulfate (potassium salt), 5-bromo-4-chloro-3-indoxyl sulfate (p-toluidine salt), 5-bromo-4- chloro-3-indoxyl thymidine-3'-phosphate (cyclohexylammonium salt) or 5-bromo-4-chloro-3-indoxyl-β-D-xylopyranoside). The inducer can be 1-O-methylglucuronic acid, isopropyl-β-D-thioglucuronic acid, isopropyl-β-D-thiogalactopyranoside, or 1-O-methyl-β-D-glucopyranoside. The indicator and corresponding inducer can be in the same layer.

The first or second layers further can include an adhesive. The first and second layers can include water impermeable substrates such as plastic, glass, or coated paper. For example, the water impermeable substrate can be polystyrene, polyethylene, polypropylene (e.g., biaxially-oriented polypropylene), or polyester. The substrates can include a contiguous piece of material having a fold whereby the first and second layers are substantially opposed to each other. The substrates can be removably or permanently attached to each other such as by a hinge, a clasp, glue, staples, or a clamp.

The microorganisms can be bacteria, fungi, yeast, phage, or mycoplasma. The bacteria can be aerobic, anaerobic or microaerophilic, and gram negative. For example, the bacteria can be E. coli, Staphylococcus, or Pseudomonas.

The invention also features a method for simultaneously propagating and obtaining replicas of a microorganism colony forming unit. The method includes applying an inoculum that includes a microorganism colony forming unit to a device to form an inoculated device, wherein the device includes a first layer that includes a gelling agent and microbial growth medium and a second layer that includes a gelling agent, wherein the first and second layers are separable from each other; contacting the first and second layers of the inoculated device to form a gel; incubating the inoculated device for a time sufficient for at least one cell division; separating the first and second layers to provide replicas of the microorganism colony forming unit; and confirming separation of the microorganism colony forming unit. The device can include an indicator and a corresponding inducer. The method further can include performing a molecular biology manipulation on at least one of the replicates.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1A depicts a device; and FIG. 1B depicts partitioning of a microorganism colony.

DETAILED DESCRIPTION

Construction of Devices

Figure 1A:
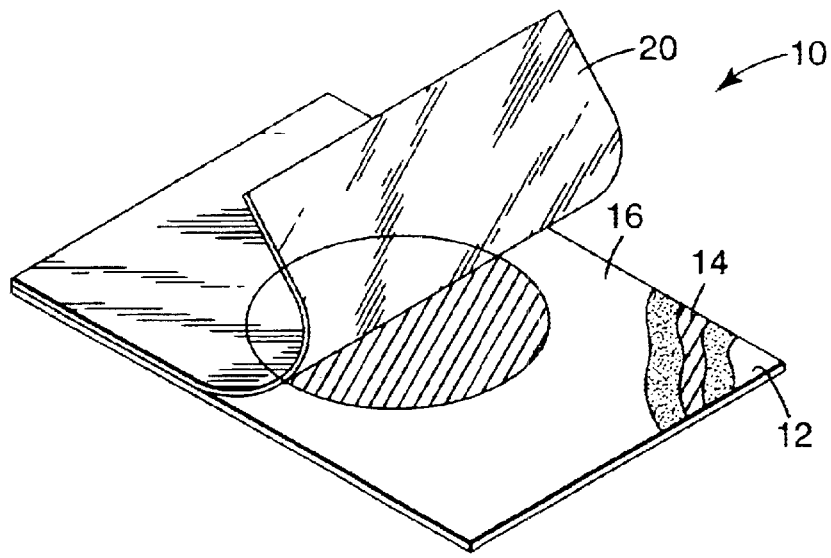
FIGS. 1A–1B are schematics that depict one embodiment of the device.

The "device" described herein contains multiple layers. As used herein, the term "layer" includes a solid substrate and any adhesives, indicators, inducers, nutrients, gelling agents, or other reagents coating the solid substrate. FIG. 1A illustrates a device suitable for use with the media of the present invention. The devices may be constructed generally as described in U.S. Pat. Nos. 4,565,783, 5,089,413, 5,232,838, and 5,601,998. The device 10 includes a first layer made from a self-supporting solid substrate, such as water impermeable substrate 12. Bottom substrate 12 typically is a relatively stiff material made of a water impermeable material that does not absorb water, such as polyester, polypropylene, polystyrene, or glass. Polyester is a particularly useful substrate. Other suitable waterproof materials include water permeable substrates such as paper containing a water impermeable polyethylene coating such as "Schoeller Type MIL" photoprint paper (Schoeller, Inc., Pulaski, N.Y.). In general, devices of the invention are constructed using substrates that are transparent or translucent to allow colonies to be viewed. In embodiments where viewing of the colonies is not necessary, opaque substrates can be used. Thickness of the substrate can range from about 0.003 in. to 0.02 in. For example, polyester films typically are about 0.004 to about 0.007 in. thick, polypropylene films are about 0.004 to about 0.008 in. thick, and polystyrene films are about 0.015 in. thick.

The upper surface of substrate 12 is coated with culture medium 14, which is then dried to provide a dry medium on substrate 12. Alternatively, adhesive may be coated on substrate 12, which serves to hold a culture medium that may be applied as a powder. The adhesive should be sufficiently transparent when hydrated to allow visualization of bacterial colonies growing on the surface of the substrate when viewed through the coated substrate. The adhesive should also be coated on the substrate at a thickness that allows the substrate to be uniformly coated with dry culture medium without completely embedding the medium in the adhesive.

A foam spacer 16 having a circular opening in the foam can be attached to the medium coated surface of substrate 12. The foam spacer covers the periphery of substrate 12, and defines an area that is to be inoculated with a sample and also serves to prevent the sample from leaking from the substrate. The diameter of the circular opening can be altered. For example, a polystyrene foam web can have 2"–2⅜" diameter die-cut circular holes and be used with the same volume of sample (approximately 1 ml). In an alternate embodiment, a device may not include a sample-containing foam spacer. In this device, the amount of sample is contained and sequestered on the substrate by the components of the medium alone.

Top cover sheet 20 is disposed on one edge of an upper surface of the foam spacer 16. Cover sheet 20 is the second layer and is preferably made of a transparent film or sheet material in order to facilitate counting of bacterial colonies present on the substrate. In addition, cover sheet 20 is preferably impermeable to bacteria and water vapor in order to avoid the risk of contamination and deterioration of the components. Materials for cover sheet 20 can be selected to provide the amount of oxygen transmission necessary for the type of microorganism to be grown. For example, polyester films have a low oxygen permeability (less than 5 g/100 in$^2$/24 hours per 0.001" of thickness) and are suitable for growing anaerobic bacteria, while polyethylene films have a high oxygen permeability (approximately 500 g/100 in$^2$/24 hours per 0.001" of thickness) and are suitable for growing aerobic bacteria. A preferred material for use as cover sheet 20 is biaxially-oriented polypropylene. The cover sheet includes gelling agents, and optionally may include microbial growth medium, inducers, indicators, and/or an adhesive.

It should be noted that the top-bottom orientation of the first and second layers can be reversed from that described above.

The first and second layers of the device can be removably or permanently attached to each other by various methods. For example, hinges, clasps, glue, tape, staples, or clamps can be used to attach the first and second layers to each other. In one embodiment, a pressure-sensitive adhesive is used to attach the first and second layers to each other.

Microbial Growth Medium

Figure 1B:
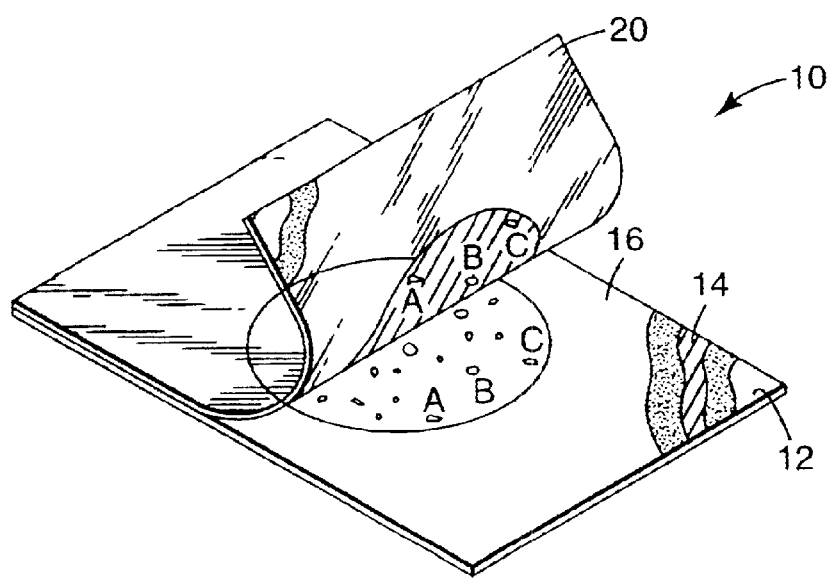

In general, the first and second layers of the device include a gelling agent in an effective amount, i.e., such that, upon separating the layers, portions of most, and preferably, of at least 80% of the visible microorganism colonies are retained on both layers of the device. In other words, at least 80% of the visible microorganism colonies partition to form replicates on the first and second layers after separating the layers. See, FIG. 1B for a diagram of the partitioning of the colony to form replicates. For example, at least 85%, 90%, 95%, or 99% of the colonies can partition and form replicates on the first and second layers. Non-limiting examples of gelling agents include guar, xanthan, locust bean gum, polyvinyl alcohol, carboxymethylcellulose, alginate, polyvinylpyrrolidone, gellan, and polyacrylic acid (low monomer content). Guar is a particularly useful gelling agent. Suitable concentrations for a gelling agent can be determined by using the methods described herein. In general, a device is produced with varying amounts of the gelling agent on the first and second layers. The device is inoculated with an aqueous sample containing microorganisms and incubated for an appropriate length of time (e.g., 16–24 hours). The layers of the device are separated, and the fraction of colonies that are retained on both the first and second layers is determined.

The first layer further includes a microbial growth medium. In some embodiments, the microbial growth medium can be on both the first and second layers. Typically, a gelling agent and microbial growth medium are applied together to the substrate included in the first layer. A suitable microbial growth medium typically contains gelling agent at a concentration of less than 1% weight/volume of solution before dehydration. For example, the gelling agent concentration before dehydration can be 0.4% to 0.9% weight/volume or 0.6% to 0.8% weight/volume. Final amounts of gelling agent in the first layer range from 20 mg to 100 mg/24 in$^2$ after drying. For example, the final amount of gelling agent can be 30 to 80 or 40 to 50 mg/24 in$^2$ in the first layer. The amount of gelling agent in the second layer typically is at least five times (5×) greater (e.g., 7×, 8×, 9×, or 10×) than the amount in the first layer. For example, the amount of gelling agent in the second layer can range from 300 to 500 mg/24 in or 400 to 450 mg/24 in$^2$.

A microbial growth medium of the invention also can include a detergent (e.g., an ionic detergent) at a concentration from about 0.5% to about 2% weight/volume of solution before dehydration. Non-limiting examples of detergents include deoxycholate, bile salts and sodium lauryl sulfate.

Additional components of the growth medium include salts, such as calcium chloride and magnesium chloride, selectable agents, indicators, and inducers. For example, selectable agents can be antibiotics such as such as kanamycin, ampicillin, carbenicillin, spectinomycin, streptomycin, vancomycin, tetracycline, or chloramphenicol. Other selectable agents can be deficiencies in particular amino acids. Indicators can be precipitable, chromogenic, or fluorescent and/or fluorogenic. Suitable fluorescent or fluorogenic indicators include, for example, 4-methylumbelliferyl phosphate (disodium salt trihydrate or free acid), 4-methylumbelliferyl-beta-D-glucopyranoside, 4-methylumbelliferyl-beta-D glucuronic acid, 4-methylumbelliferyl-beta-D-galactopyranoside, fluoroscein diacetate, or fluoroscein antibody conjugates. A precipitable indicator can be, for example, 2,3,5-triphenyltetrazolium chloride. Chromogenic indicators typically are colorless until activation by the microorganism, e.g., enzymatic hydrolysis or reduction of a chemical bond. Non-limiting examples of chroimogenic indicators include 5-bromo-4-chloro-3-indoxyl-β-D-glucuronic acid, L-Alanine-5-bromo-4-chloro-3-indoxyl ester (trifluoroacetate salt), 5-bromo-4-chloro-3-indoxyl-1-acetate, 5-bromo-4-chloro-3-indoxyl-3-acetate, 5-bromo-4-chloro-3-indoxyl-N-acetyl-β-D-galactosaminide, 5-bromo-4-chloro-3-indoxyl-N-acetyl-α-D-glucosaminide, 5-bromo-4-chloro-3-indoxyl butyrate, 5-bromo-4-chloro-3-indoxyl caprylate, 5-bromo-4-chloro-3-indoxyl-β-D-cellobioside, 5-bromo-4-chloro-3-indoxyl-α-L-fucopyranoside, 5-bromo-4-chloro-3-indoxyl-β-D-fucopyranoside, 5-bromo-4-chloro-3-indoxyl-β-L-fucopyranoside, 5-bromo-4-chloro-3-indoxyl-α-D-galactopyranoside, 5-bromo-4-chloro-3-indoxyl-α-D-galactopyranoside, 5-bromo-4-chloro-3-indoxyl-α-D-glucopyranoside, 5-bromo-4-chloro-3-indoxyl-α-D-glucopyranoside, 5-bromo-4-chloro-3-indoxyl-β-D-glucuronic acid (cyclohexylammonium salt), 5-bromo-4-chloro-3-indoxyl-β-D-glucuronic acid (sodium salt), 5-bromo-4-chloro-3-indoxyl myo-inositol-1-phosphate (ammonium salt), 5-bromo-4-chloro-3-indoxyl-α-D-maltotriose, 5-bromo-4-chloro-3-indoxyl myristate, 5-bromo-4-chloro-3-indoxyl-α-D-mannopyranoside, 5-bromo-4-chloro-3-indoxyl-nonano ate, 5-bromo-4-chloro-3-indoxyl oleate, 5-bromo-4-chloro-3-indoxyl palmitate, 5-bromo-4-chloro-3-indoxyl phosphate (di{2-amino-2-methyl-1,3-propanediol}salt), 5-bromo-4-chloro-3-indoxyl phosphate (dilithium salt hydrate), 5-bromo-4-chloro-3-indoxyl phosphate (dipotassium salt), 5-bromo-4-chloro-3-indoxyl phosphate (disodium salt sesquihydrate), 5-bromo-4-chloro-3-indoxyl phosphate (potassium salt), 5-bromo-4-chloro-3-indoxyl phosphate (p-toluidine salt), 5-bromo-4-chloro-3-indoxyl sulfate (potassium salt), 5-bromo-4-chloro-3-indoxyl sulfate (p-toluidine salt), 5-bromo-4-chloro-3-indoxyl thymidine-3'-phosphate (cyclohexylammonium salt), or 5-bromo-4-chloro-3-indoxyl-β-D-xylopyranoside. Sodium tellurite also is a suitable indicator.

Inducers stimulate an enzyme to cleave a corresponding indicator. For example, 1-O-methylglucuronic acid is an inducer that stimulates glucoronidase to cleave 5-bromo-4-chloro-3-indoxyl-β-D-glucuronic acid (indicator) to produce a colored product. Other inducer and indicator pairs include 5-bromo-4-chloro-3-indoxyl-β-D-glucuronic acid, sodium salt or 3-indoxyl-β-D-glucuronic acid, sodium salt and isopropyl-β-D-thioglucuronic acid, sodium salt; 5-bromo-4-chloro-3-indoxyl-β-D-galactopyranoside or -indoxyl-β-D-galactopyranoside and isopropyl-β-D-thiogalactopyranoside; and 5-bromo-4-chloro-3-indoxyl-β-D-glucopyranoside, 3-indoxyl-β-D-glucopyranoside, or 5-bromo-6-chloro-3-indoxyl-β-D-glucopyranoside and 1-O-Methyl-β-D-glucopyranoside.

A further embodiment of the present invention includes a lac differentiation mechanism. Because the device includes two chromogenic indicators, the β-galactosidase deficient colonies activate a first indicator and the β-galactasidase producing colonies activate a second indicator, thereby producing two color differentiation.

Use of Devices for Propagation or Storage of Microorganisms

In use, a predetermined amount of inoculum, typically about one ml of inoculum, is added to the device illustrated in FIG. 1A by pulling back cover sheet 20 and adding an aqueous test sample or water to the middle of substrate 12. Cover sheet 20 is then replaced over substrate 12 and the inoculum is evenly spread on the substrate. A convenient tool to do this is a weighted circular template, which also is used to confine the inoculum to a specific area of substrate 12. As the inoculum contacts and is spread on substrate 12, the culture medium on substrate 12 hydrates to form a growth-supporting nutrient gel. The inoculated device is then incubated for a predetermined time after which the number of bacterial colonies growing on the substrate may be counted through the transparent cover sheet 20.

A variety of microorganisms can be propagated or stored with the device of the invention. Suitable microorganisms include bacteria, fungi, yeast, phage, and mycoplasma. Bacteria can be aerobic, anaerobic, or microaerophilic, and can be gram negative or gram positive. For example, the bacteria can be *Escherichia coli*, Staphylococcus, Salmonella, or Pseudomonas. Microbial growth medium used in the device of the invention can be adjusted to account for particular needs of each microorganism.

Current techniques for plating microorganisms containing recombinant DNA are improved by the plating medium and methods described herein. The unique formulation of gelling agent and microbial growth medium with inducer and indicator used in the device of the invention provides, after incubation for an appropriate period of time, microorganism colonies that are larger than colonies growing on commercially available Petrifilm™ plates (3M, St. Paul, Minn.) that are currently available, after the same length of incubation. Furthermore, upon separating the first and second layers of the plate, microorganism colonies partition to form replicates on the first and second layers. Thus, a portion of a colony is retained on the first layer and a portion of the same colony is retained on the second layer. The portion of colony on each film is viable and can be detected by magnified or unmagnified visual inspection. This feature facilitates use of a portion of each colony to perform genetic or biochemical analyses, while preserving an exact genetic duplicate of the colonies for storage or further analyses. Genetic and biochemical analyses can include, for example, hybridization, polymerase chain reaction, plasmid restriction digest analysis, DNA sequencing, or expression screening techniques such as antibody-mediated expression screening. For example, colony blotting/lifting techniques can be carried out using colonies retained on one film (e.g., the second layer), while retaining the colony replicates in the other film.

Thus, the present invention allows a microorganism colony forming unit to be simultaneously propagated and replicated. As used herein, "colony forming unit" refers to at least one cell, and can include an aggregation of cells, such as a colony. In general, an inoculum containing the colony forming unit is applied to the device, then the first layer and second layers are contacted to form a gel. The colony forming unit is grown under appropriate conditions for a time sufficient for at least one cell division to occur, then the first and second layers are separated to provide replicas of the microorganism colony forming unit.

The device of the invention avoids problems associated with agar plates in that it can be stored in the refrigerator or freezer with less risk of dehydration, disintegration of the gel, or cross-contamination of the colonies. Such features are provided by the sealable configuration of the device, coupled with the unique gelling properties of the medium. Thus, a microorganism colony forming unit can be preserved by sealing the first and second layers of the device. Typically, the colony forming unit is incubated under conditions suitable for at least one cell division before preservation. Colony forming units are preserved by storing the device under conditions where cell division is inhibited (e.g., in refrigerator).

The invention will be further described in the following examples, which do not limit the scope of the invention described in the claims.

EXAMPLES

Example 1

Composition of colony replicating and storage device: Gen-1A, Gen-1B, and Gen-2 plates were constructed as an article, similar to the Petrifilm ™ *E. coli* Count plates. See, for example, U.S. Pat. No. 4,565,783. The rectangular plates were approximately 4"×3", with a 2" diameter circular plating area. The uncoated films that were used had an approximate thickness of about 0.4 to about 3 mil. The first layer (in this case, the top film) had an approximate thickness of approximately 0.6 mil and the second or bottom layer had an approximate thickness of about 2 mm.

The top layers of the Gen-1A and 1B plates consisted of biaxially-oriented polypropylene (BOPP) coated with RD1272 adhesive (96:4 iso-octyl acrylate:acrylamide, coated to 195 mg/200 cm$^2$), which was powder-coated with a mixture (109.5:1 weight ratio) of Meyprogat 150 guar gum (as described in U.S. Pat. No. 4,565,783) and Cabosil (coated to 219 mg/24 in$^2$). After coating, there was approximately 16.7 mg guar/in$^2$. The top layer for the Gen-2 plate was the same top layer including triphenyltetrazolium chloride in the adhesive layer, as the commercially available Petrifilm *E.coli* Count Plate (catalog #6414, 3M Company, St. Paul, Minn.).

The nutrient/inhibitor compositions shown in Table 1, were coated and dried onto a adhesive-coated paper bottom films for Gen-1A and Gen-2 or a Melinex polyester (DuPont, Wilmington, Del.) film for Gen-1B. The dry weight of the coated broth mixture was 12.5 mg/in$^2$ for all three plates. The formulations shown in Table 1 were designed for rehydration using an approximately 1 ml sample of microorganisms.

TABLE 1

| | Solution Weight (%) | |
|---|---|---|
| Component | Gen-1A and 1B | Gen-2 |
| Deionized water | 87.5 | 87.5 |
| Yeast Extract, Peptone A, Peptone G* | 10.7 | 10.7 |
| Guar | 0.59 | 0.59 |
| Deoxycholic Acid, sodium salt | 0.96 | 0.96 |
| Calcium chloride | 0.04 | 0.04 |
| Magnesium chloride | 0.01 | 0.01 |
| 5-bromo-4-chloro-3-indoxyl-β-D-glucuronic acid, sodium salt | 0.1 | — |
| 1-O-methylglucuronic acid, sodium salt | 0.1 | — |
| 5-bromo-4-chloro-3-indoxyl-β-D-galacto-pyranoside | — | 0.2 |
| Isopropyl-b-D-galactopyranoside | — | 0.05 |

* Mixed in a 6:1:12.99 weight ratio.

A polystyrene foam web (20 mil thick, coated on the underside with adhesive), with 2"-diameter die-cut circular holes, was adhered to the broth coated surface of the bottom films to form a "foam dam" on the Gen-1A, Gen-1B, and Gen-2 plates. The devices were cut into 4"-long×3"-wide rectangles, with the 2" diameter hole exposing the broth-coated bottom film (roughly centered in the rectangular plate). Double-stick tape (⅜"-wide) was applied to one of the 3" edges of the rectangle and was used to fasten the guar-coated top film to the polystyrene foam web to complete the construction of the plates.

Example 2

Recovery of viable cells from each layer of the Gen-1A: plate plates constructed as described in Example 1 were inoculated with *E. coli* strain P16. The inoculum was prepared by putting a colony into 5 ml of tryptic soy broth (Remel, Inc., Lenexa, Kans.) and incubating the culture overnight at 37° C. The inoculum was diluted serially (1:100) to a final dilution of $10^{-8}$. One ml of the final dilution was inoculated onto each of two Gen-1A plates according to the standard procedure for inoculating commercially available *E. coli*/Coliform Count Petrifilm™ plates. The plate was incubated overnight (18 hrs) at 37° C. One of the plates, containing 13 colonies was used for the test. The plate was opened and the two layers were carefully separated. It was observed that part of each colony transferred to both of the layers. The layers were placed onto the bench with the colonies facing up. Six colonies were randomly chosen. Separate sterile disposable inoculating loops (Difco; Detroit, Mich.) were used to pick colony material from each selected colony on both films. The colony material was used to inoculate a small spot on a tryptic soy agar plate (Remel). The plate was incubated at 37° C. for 24 hours and examined for colony growth. After incubation, all spots on the tryptic soy agar plate showed growth, indicating the presence of viable cells retained on both films of the plate.

Example 3

Recovery of genetic material from each layer of the Gen-1B plate: Plates constructed as described in Example 1 were used in this experiment. *E. coli* strain DH5α was used in all experiments. The cells were made competent using $CaCl_2$ and transformed with the plasmid puc-gfp3. Puc-gfp3 is a Puc19 derivative containing a gene encoding green fluorescent protein. After transformation and recovery, the cells were diluted in Butterfield?s buffer (Hardy Diagnostics; Santa Clara, Calif.) containing ampicillin (50 g/ml) and 1 ml of the diluent was plated on Gen-1B plates. The plates were incubated at 37° C. for 14 to 18 h. The colonies were randomly chosen before the devices were opened, the top and bottom layers were marked with a circle around the selected colonies, and the device was opened.

Plasmid isolation Plasmid preparations were made from the colony replicates on each of the layers. A sterile toothpick was used to transfer material from each colony replicate into 5 ml of Luria-Bretani (LB) agar containing ampicillin (100 µg/ml) and grown for 16 h at 37° C. with shaking (200 rpm). The plasmid preps were made from four different colonies from the top and bottom films of the plate. The optical density of the cultures was measured at $OD_{600}$ after overnight growth and the optical density between the cultures from top and bottom film were similar. The DNA was isolated from 5 ml of culture by the alkaline lysis method using the Wizard Miniprep kit (Promega, Madison, Wisc.). The plasmids were cut with EcoRI and electrophoresed through a 0.7% agarose gel. The results indicated that plasmid DNA was obtained from every selected colony replicate on the top and bottom layers of the plate.

Colony PCR Colonies were selected and labeled as described above. After separation of the layers, each colony replicate was suspended in 25 µl of AmpliTaq gold PCR (PE Biosystems, Foster City, Calif.) or Qiagen PCR MasterMix (Qiagen, Inc., Valencia, Calif.) cocktail and PCR was carried out for 40 cycles in a Perkin-Elmer 9700 thermocouple. The experiment was repeated twice with five colonies from both the bottom and top layers. After PCR, the products were electrophoresed through a 0.7% agarose gel. Ethidium bromide staining indicated that the amount of products from PCR from each of the five colonies from either the top or bottom layers were similar. The results also indicated that the same PCR amplification product was obtained from all of the reactions set up from colony replicates taken from the top and bottom layers.

Example 4

Prophetic Example of Storage of *E. coli* colonies on Gen-1A, Gen-1B, and Gen-2 Plates: Transformed *E. coli* cells are plated on LB agar plates and on plates described herein. The plates are incubated at 37° C. for 18 hours. After incubation, the plates are placed in resealable (ZipLock™) plastic bags and placed at −20° C. After storage at freezer temperature for at least one week, the plates are removed from the freezer and allowed to warm to room temperature. The colonies are picked with a sterile loop for (a) subculturing the colonies into broth medium (e.g. LB broth) and (b) for polymerase chain reaction (PCR) analysis of the genetic material within the colonies.

The colonies will be preserved during the freeze/thaw cycles to avoid cross-contamination of the clones. This will allow the user to pick the colonies for subculturing quite easily after the plates have been thawed. Furthermore, because the colonies are growing within the culture medium, rather than on the surface of the culture medium, there is less likelihood that the genetic material within the colonies will become cross-contaminated during the freeze/thaw cycles.

In contrast, freezing agar plates with the surface colonies, will lead to the accumulation of ice crystals on the surface of the agar. When the plates are allowed to thaw, this surface moisture will cause adjacent colonies to cross-contaminate, thereby ruining the purity of subcultures and the genetic integrity of the nucleic acid materials isolated from colonies for PCR or other genetic analyses. Furthermore, the longer the agar remains at the frozen temperature, the higher the likelihood that cracks will form in the agar due to dehydration of the gel. These cracks provide additional surfaces for the condensation and coalescence of moisture during the thawing cycle, which increases the possibility of colony disintegration and cross-contamination.

Example 5

Effect of plate composition on colony size: The objective of this experiment was to compare the growth of plasmid-bearing *E. Coli* strains on the plates described herein with other commercial dry-film media. After incubation, the growth was compared as a function of the average colony size on each plate.

Inoculum was prepared by adding ampicillin (Sigma Chemical Company, St. Louis, Mo., final concentration of 50 µg/mL) to a tube containing 4.5 mL of Tryptic Soy Broth (Remel, Inc., Lenexa Kans.) A colony of *E. coli* DH10B, transformed with pGFP3, was inoculated into the tube and the culture was incubated overnight at 37° C. without shaking.

After incubation, the tube was mixed by vortex action to achieve a homogeneous suspension. The suspension was serially diluted in Butterfield's Buffer (Hardy Diagnostics; Santa Clara, Calif.) to a final dilution of $10^{-7}$.

In addition to the plates described herein, the following commercial Petrifilm™ plates were inoculated: *E. coli* Count (EC), Coliform Count (CC), Enterobacteriaceae Count (EB), Rapid Coliform Count (RCC), and Aerobic Count (AC). All of the plates are available from 3M Company (St. Paul, Minn.).

Plates were inoculated according to the Petrifilm plate product insert with 1.0 mL of the diluted cell suspension. The Petrifilm plate spreader (3M Company, St. Paul, Minn.) was used to distribute the inoculum within the plating area.

Inoculated plates were placed in stacks of 8–12 and incubated at 37° C. for 16 hours. The incubated plates were scanned on a Hewlett-Packard ScanJet 6100C flatbed scanner. The images were viewed on an IBM 300PL computer with "Imaging for Windows NT" software (Wang Laboratories, Inc.; Billerica, Mass that individual pixels could be seen.

Colony size was estimated by determining the dimensions (in pixels) of individual colonies. Colonies were red on all plates except the Gen-1 and EC formulations, where the colonies were blue. When determining colony size on the EB plates, gas bubbles surrounding the colonies were not counted as a part of the colony diameter. The number of pixels in an average colony was calculated (Table 2). Colonies that superimposed the yellow grid on the plates were not used for the colony size estimates. The number of colonies used in each analysis is indicated in Table 2. In Table 2, "*" refers to small acid zones that were visible on the CC plate after 16 hours of incubation, but colonies in the center of the zones were not visible, and "**" refers to only one colony that was visible on the EC plate after 16 hours of incubation. This colony was superimposed over one of the yellow grid lines and, therefore was not included in the analysis.

TABLE 2

| Plate Type | Colony Size (pixels) | Number of colonies | Range (pixels) |
|---|---|---|---|
| AC | 5.8 ± 2.6 | 12 | 2–9 |
| CC | * | * | * |
| EB | 11.8 ± 3.4 | 6 | 9–16 |
| EC | ** | ** | ** |
| Gen-IA | 41.2 ± 9.9 | 9 | 25–56 |
| Gen-2 | 19.1 ± 3.1 | 8 | 16–25 |
| RCC | 4.1 ± 2.2 | 8 | 2–9 |

These data show that the apparent colony size of the Gen-1A and Gen-2 formulations is larger than the other Petrifilm plates tested. The average colony size on the Gen-1A formulation was the largest of all of the plates tested. The relatively small number of colonies on each plate results in less competition for nutrients on the plates. Thus, at the incubation temperature used for these experiments, the colonies were growing optimally in each formulation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for the propagation or storage of microorganisms comprising:
    a first layer that comprises a galling agent and microbial growth medium;
    a second layer that is separable from the first layer and comprises a gelling agent in an amount effective to partition at least 80% of visible microorganism colonies grown on the device to form replicates on the first and second layers when the first and second layers are separated;
    an indicator on the first layer or the second layer; and
    a corresponding inducer on the first layer or the second layer.

2. The device of claim 1, further comprising replicates of microorganisms colonies on said first or second layer are detectable by magnified or unmagnified visual inspection.

3. The device of claim 1, further comprising replicates of microorganism colonies on said first or second layer that are detectable by genetic analysis.

4. The device of claim 3, wherein at least one replicate can be detected by hybridization, polymerase chain reaction, plasmid restriction analysis, or expression screening.

5. The device of claim 1, further comprising viable replicates of microorganism colonies on the first layer, the second layer, or both.

6. The device of claim 1, wherein said first or second layers are rehydratable.

7. The device of claim 1, wherein said gelling agent of said first or second layers is guar gum, xanthan gum, locust bean gum, polyvinyl alcohol, carboxymethyl-cellulose, alginate, polyvinylpyrolidone, gellan or low monomer content polyacrylic acid.

8. The device of claim 1, wherein said gelling agent of said first or second layers is guar gum.

9. The device of claim 1, wherein said microbial growth medium comprises a detergent.

10. The device of claim 9, wherein said detergent is an ionic detergent.

11. The device of claim 10, wherein said ionic detergent is deoxycholate, bile salts or lauryl sulfate.

12. The device of claim 1, wherein said microbial growth medium comprises a salt.

13. The device of claim 1, wherein said first layer further comprises a selectable agent.

14. The device of claim 13, wherein said selectable agent is an antibiotic.

15. The device of claim 13, wherein said selectable agent is an amino acid deficiency.

16. The device of claim 1, wherein said indicator is precipitable.

17. The device of claim 16, wherein said indicator is chromogenic.

18. The device of claim 17, wherein said chromogenic indicator is 5-bromo-4-chloro-3-indoxyl-β-D-glucuronic acid, L-Alanine-5-bromo-4-chloro-3-indoxyl ester (trifluoroacetate salt), 5-bromo-4-chloro-3-indoxyl-1-acetate, 5-bromo-4-chloro-3-indoxyl-3-acetate, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl butyrate, 5-bromo-4-chloro-3-indoxyl caprylate, 5-bromo-4-coloro-3-indoxyl-β-D-cellobioside, 5-bromo-4-chloro-3-indoxyl-α-L-fucopyranoside, 5-bromo-4-chloro-3-indoxyl-β-D-fucopyranoside, 5-bromo-4-chloro-3-indoxyl-β-L-fucopyranoside, 5-bromo-4-chloro-3-indoxyl-α-D-galactopyranoside, 5-bromo-4-chloro-3-indoxyl-β-D-galactopyranoside, 5-bromo-4- chloro-3-indoxyl-α-D-glucopyranoside, 5-bromo-4-chloro-3-indoxyl-β-D-glucopyranoside, 5-bromo-4-chloro-3-indoxyl-β-D-glucuronic acid(cyclohexylammonium salt), 5-bromo-4-chloro-3-indoxyl-α-D-glucuronic acid (sodium salt), 5-bromo-4-chloro-3-indoxyl myo-inositol-1-phosphate (ammonium salt), 5-bromo-4-chloro-3-indoxyl-α-D-maltotriose, 5-bromo-4-chloro-3-indoxyl myristate, 5-bromo-4-chloro-3-indoxyl-α-D-mannopyranoside, 5-bromo-4-chloro-3-indoxyl-nonanoate, 5-bromo-4-chloro-3-indoxyl oleate, 5-bromo-4-chloro-3-indoxyl paemitate, 5-bromo-4-chloro-3-indoxyl phosphate (di-{2-amino-2-methyl-1,3-propanediol}salt), 5-bromo-4-chloro-3-indoxyl phosphate (dilithium salt hydrate), 5-bromo-4-chloro-3-indoxyl phosphate (dipotassium salt), 5-bromo-4-chloro-3-indoxyl phosphate (disodium salt sesquihydrate), 5-bromo-4-chloro-3-indoxyl phosphate (potassium salt), 5-bromo-4-chloro-3-indoxyl phosphate (toluidine salt), 5-bromo-4-chloro-3-indoxyl sulfate (potassium salt), 5-bromo-4-chloro-3-indoxyl sulfate (p-toluidine salt), 5-bromo-4-chloro-3-indoxyl thymidine-3'-phosphate (cyclohexylammonium salt) or 5-bromo-4-chloro-3-indoxyl-β-D-xylopyranoside.

19. The device of claim 1, wherein said inducer is 1-O-methylglucuronic acid, isopropyl-β-D-thioglucuronic acid, isopropyl-β-D-thiogalactopyranoside, or 1-O-methyl-β-D-glucopyranoside.

20. The device of claim 1, wherein said first or second layers further comprise an adhesive.

21. The device of claim 1, wherein said first and said second layers comprise water impermeable substrates.

22. The device of claim 21, wherein said water impermeable substrate is plastic, glass, or coated paper.

23. The device of claim 21, wherein said water impermeable substrate is polystyrene, polyethylene, polypropylene, or polyester.

24. The device of claim 23, wherein said polypropylene is a biaxially-oriented polypropylene.

25. The device of claim 21, wherein said substrates comprise a contiguous piece of material having a fold whereby said first and second layers are substantially opposed to each other.

26. The device of claim 22, wherein said substrates are removably or permanently attached to each other.

27. The device of claim 26, wherein said substrates are attached to each other by a hinge, a clasp, glue, staples, or a clamp.

28. The device of claim 1, further comprising at least one colony of microorganisms that comprises bacteria, fungi, yeast, phage, or mycoplasma.

29. The device of claim 28, wherein said bacteria are aerobic, anaerobic or microaerophilic.

30. The device of claim 28, wherein said bacteria are gram negative.

31. The device of claim 28, wherein said bacteria are *E coli*, Staphylococcus, or Pseudomonas.

32. The device of claim 1, wherein the second layer comprises gelling agent in an amount effective to partition at least 85% of visible microorganism colonies grown on the device to form replicates on the first and second layers when the first and second layers are separated.

33. The device of claim 1, wherein the second layer comprises gelling agent in an amount effective to partition at least about 95% of visible microorganism colonies grown on the device to form replicates on the first and second layers when the first and second layers are separated.

34. The device of claim 1, wherein said second layer further comprises a microbial growth medium.

35. The device of claim 1, wherein said indicator and said corresponding inducer are in the same layer.

36. A method for simultaneously propagating and obtaining replicas of a microorganism colony forming unit comprising, a) applying an inoculum comprising a microorganism colony forming unit to a device to form an inoculated device, said device comprising a first layer comprising a gelling agent and microbial growth medium and a second layer that is separable from the first layer and comprises a gelling agent in an amount effective to partition at least 80% of visible microorganism colonies grown on the device to form replicates on the first and second layers with the first and second layers are separated;

b) contacting said first and second layers of said inoculated device to form a gel;

c) incubating said inoculated device for a time sufficient for at least one cell division;

d) separating said first and second layers to provide replicas of said microorganism colony forming unit; and e) confirming separation of said microorganism colony forming unit.

37. The method of claim 36, wherein said first or said second layers further comprise an indicator and a corresponding inducer.

38. The method of claim 30, wherein said method further comprises performing a molecular biology manipulation on at least on said replicate.

* * * * *

UNITED STATES PATENT AND TRADEMARK OFFICE
CERTIFICATE OF CORRECTION

PATENT NO.    : 6,649,406 B1
DATED         : November 18, 2003
INVENTOR(S)   : Michael G. Williams, Karen E. Hesselroth and Raj Rajagopal It is certified that error appears in the above-identified patent and that said Letters Patent is hereby corrected as shown below:

Column 2,
Line 52, delete "glucuronicacid" and insert in place thereof -- glucuronic acid --.

Column 5,
Line 54, delete "500 mg/24 in" and insert in place thereof -- 500 mg/24 in$^2$ --.

Column 6,
Line 17, delete "N-acetyl-α-D-glucosaminide" and insert in place thereof
-- N-acetyl-β-D-glucosaminide --.
Line 24, delete "indoxyl-α-D-galactopyranoside" and insert in place thereof
-- indoxyl-β-D-galactopyranoside --.
Line 26, delete "3-indoxyl-α-D-glucopyranoside" and insert in place thereof
-- 3-indoxyl-β-D-glucopyranoside --.

Column 8,
Line 63, delete "Isopropyl-b-D-galactopyranoside" and insert in place thereof
-- Isopropyl-β-D-thiogalactopyranoside --.

Column 9,
Line 13, delete "plate plates" and insert in place thereof -- plate: Plates --.
Line 47, delete "Butterfields?s" and insert in place thereof -- Butterfield's --.
Line 48, delete "(50 g/ml)" and insert in place thereof -- (50 µg/ml --.

Column 10,
Line 8, delete "thermocouple" and insert in place thereof -- thermocycler --.

Column 11,
Line 20, after "Mass" insert -- The images were enlarged to 1000% so --.

Column 12,
Line 4, delete "galling" and insert in place thereof -- gelling --.
Line 16, delete "layer are" and insert in place thereof -- layer that are --.
Line 62, delete "5-bromo-4-coloro-3-" and insert in place thereof
-- 5-bromo-4-chloro-3 --.

UNITED STATES PATENT AND TRADEMARK OFFICE
CERTIFICATE OF CORRECTION

PATENT NO. : 6,649,406 B1
DATED : November 18, 2003
INVENTOR(S) : Michael G. Williams, Karen E. Hesselroth and Raj Rajagopal It is certified that error appears in the above-identified patent and that said Letters Patent is hereby corrected as shown below:

Column 13,
Line 4, delete "-α-D-" and insert in place thereof -- -β-D- --.
Line 10, delete "paemitate," and insert in place thereof -- palmitate --.
Line 17, delete "(toluidine" and insert in place thereof -- (p-toluidine --.

Column 14,
Line 47, delete "30" and insert in place thereof -- 36 --.

Signed and Sealed this

Eleventh Day of May, 2004

JON W. DUDAS
*Acting Director of the United States Patent and Trademark Office*